United States Patent
Felisaz et al.

(10) Patent No.: US 6,599,534 B2
(45) Date of Patent: *Jul. 29, 2003

(54) MASKING AGENT IN POWDER FORM FOR PHARMACEUTICAL TASTES

(75) Inventors: Denis Felisaz, Annemasse (FR); Yvan Jacquier, Geneva (CH)

(73) Assignee: Pancosma Societe Anonyme pour l'Industrie des Produits, Grand-Saconnex (CH)

( * ) Notice: Subject to any disclaimer, the term of this patent is extended or adjusted under 35 U.S.C. 154(b) by 11 days.

This patent is subject to a terminal disclaimer.

(21) Appl. No.: 10/003,569

(22) Filed: Oct. 24, 2001

(65) Prior Publication Data

US 2002/0058070 A1 May 16, 2002

Related U.S. Application Data

(63) Continuation-in-part of application No. 09/555,813, filed as application No. PCT/IB98/01915 on Dec. 2, 1998.

(30) Foreign Application Priority Data

Dec. 3, 1997 (EP) .............................. 97810941

(51) Int. Cl.⁷ .............................. A61K 9/14; A61K 9/20
(52) U.S. Cl. ...................... 424/489; 424/464; 424/484; 424/485; 424/400
(58) Field of Search ................................ 424/489, 464, 424/484, 485, 400

(56) References Cited

U.S. PATENT DOCUMENTS 4,828,857 A * 5/1989 Sharma et al. .............. 426/285

FOREIGN PATENT DOCUMENTS

| DE | 1 9617487 | 11/1997 |
|---|---|---|
| DE | 19639343 | 4/1998 |

* cited by examiner

*Primary Examiner*—Carlos Azpuru
*Assistant Examiner*—Robert M. Joynes
(74) *Attorney, Agent, or Firm*—Sturm & Fix LLP

(57) ABSTRACT

A masking agent for pharmaceutical tastes comprises a mixture of a sapid agent and an enhancer, in the form of an intimate mixture. The sapid agent/enhancer distribution is substantially homogeneous and non-statistical. The proportion of sapid agent relative to the enhancer is substantially constant and equal in all powder particles. The masking agent can have a grain size comprised between 10 and 100 μm, with a Gaussian distribution. The proportion of sapid agent/enhancer is comprised between 97/3 and 90/10, expressed in parts by weight. The sapid agent comprises a sweetener selected from the group comprising sodium saccharinates, calcium saccharinates, saccharine, aspartylphenylalanine, acesulfam, cyclamates, stevioside, and mixtures thereof; and the enhancer is selected from the group comprising thaumatin, neohesperidin dihydrochalcone (NHDC), glycyrrhizin, and mixtures thereof. A method of producing a masking agent is also disclosed.

18 Claims, No Drawings

MASKING AGENT IN POWDER FORM FOR PHARMACEUTICAL TASTES

CROSS-REFERENCE TO RELATED APPLICATIONS

This application is a Continuation-In-Part of U.S. patent application Ser. No. 09/555,813 filed Jul. 24, 2000, which was filed in the U.S. as the national phase of International Patent Application No. PCT/IB98/01915 filed Dec. 2, 1998, which claimed priority of European Application No. 97810941.1 filed Dec. 3, 1997, entitled "Masking Agent in Powder Form for Pharmaceutical Flavours", all of which are including in their entirety by reference made hereto.

BACKGROUND OF THE INVENTION

1. Field of the Invention

The present invention relates to a masking agent in powder form intended to mask unpleasant pharmaceutical tastes of medicaments whenever necessary.

2. Description of the Prior Art

Traditionally, masking agents for unpleasant pharmaceutical tastes are used whenever the patient, especially a young child, has to take the medicament orally. The substances used are of various types and are generally added to the pharmaceutical formulation as an excipient. For example, we can cite sweeteners including saccharine and its derivatives.

Numerous studies on this subject aim more particularly to discover and exploit new substances rather than the way in which such substances can be incorporated in the final pharmaceutical composition. Numerous patents can be cited for example EP 0 351 566, EP 0 350 667, EP 0 351 567, relating to a taste modifier derived from a vegetable *Curculigo latifolia* called curculin, or EP 0 753 296 which indicates how to make an anti-inflammatory steroid, ibuprofen, which has a particularly strong bitter taste.

However, the principal problem is not to find new chemical substances, either natural or synthetic, for masking unpleasant tastes, but rather to develop the manner in which these new or known masking agents will be used.

It is in fact important that the masking effect should be constant and uniform from one administration of the medicament to the next, failing which the sought-after effect with the patient could not be guaranteed. This is precisely not so with traditional masking agents that are either powders statistically distributed in the final medicament formulation, or statistical mixtures of powders.

This is in particular the case when the masking agent contains a sweetener as sapid agent and a potentiator (or enhance) having very different particle sizes, namely a powder of a sweetener having a relatively large grain size mixed with a potentiator in the form of a much finer powder. The sweetener, that is to say the agent which provides the sweet taste, is usually saccharine or sodium or calcium saccharinate which themselves have a bitter of metallic taste, or sometimes other intense sweeteners of natural or synthetic origin.

The primary role of the sweetener or more generally of the sapid agent is to replace the unpleasant pharmaceutical taste of the final medicament.

The potentiator (or reinforcer, or enhancer) has a double role. Firstly, as its name indicates, it has the effect of extending the time of the perception of the taste of the sapid agent which, in its absence, would be too short. A good potentiator, as those classically used, allows for example an increase of the perception time, in particular the sweetness perception time (by 4 to 5 times). The other effect of the potentiator, and not the least, is to hide the secondary or parasitic taste of the sweetener, e.g. the bitter, metallic taste of saccharine or its sodium or calcium salts.

To avoid any ambiguity in the terminology used herein, we will used the term "masking agent" to designate the mixture of the sapid agent/potentiator, which is the subject of this invention, as well as traditional corresponding products serving for comparative purposes, whereas we will use the expression "masking formulation" or "masking premix", when the masking agent itself is dispersed in a support.

Traditional masking agents of the sapid agent/potentiator type are statistical mixtures of one or more sweeteners and of one or more potentiators which have, as stated before, very different particles sizes, In spite of the care which can be brought to their realization, this can only result in very heterogeneous mixtures. They will therefore be named hereafter "coarse masking agents".

DETAILED DESCRIPTION OF THE INVENTION

The problems evoked hereinabove are solved by the invention, in a surprisingly simple way, the invention consisting in proposing a powdered masking agent for pharmaceutical tastes in the form of an intimate mixture of a sapid agent and a potentiator. This mixture is in the form of an intimate mixture with a substantially uniform, non-statistical sapid agent/potentiator distribution, and wherein the proportion of sweetener to potentiator is substantially constant in all particles.

When reference is made to "a sapid agent", or "a potentiator", it should be understood that this is intended to comprehend "at least one sapid agent", or "at least one potentiator", respectively.

Preferably, the powdered masking agent according to the invention has a particle size comprised between 10 and 100 μm, with a Gaussian distribution. Preferably too, the proportion sapid agent/potentiator(s) is comprised between 97/3 and 90/10, expressed in parts by weight.

Particles are substantially spherical in shape and they do not segregate in bags. Their density is individually above 1, whereas the powder itself, due to the empty spaces between particles, has an apparent density between 0.7 and 0.8.

As indicated above and as will be seen below, because the proportion of sapid agent to sweetener is substantially constant and equal from one particle to the other, it will be constant from one granule to the other in the masking formulation wherein the masking agent is dispersed in a support, and consequently in the final medicament. This guarantees for the patient not only an acceptable taste, but above all a constant taste from one administration of the medicament to another administration.

According to one of the preferred embodiments of the invention, the masking agent according to the invention can be a powder with a Gaussian distribution and a mean particle diameter comprised between 10 and 100 μm, comprising between 65,000,000 and 85,000,000, for example around 75,000,000 particles per gram, compared to saccharine of 40–80 mesh having a particle size comprised between 100 and 1000 μm and comprising only 50,000 to 70,000, with a mean of about 60,000 particles per gram.

As sapid agent, a sweetener can be used or other substances such as methyl-, ethyl- or carboxyl(m)ethylcelluloses, pectins, carraghenates or alginates, all of which are able to excise an effect on the taste buds. Advantageously, one of several sweeteners will be used, for example sodium or calcium saccharinate or saccharine, already mentioned above, as well as other sweeteners such as aspartyl-phenylalanine, acesulfam and cyclamates and stevioside which is a glycoside of natural origin.

As potentiators, one can use thaumatin, which is a protein of vegetable origin, and glycosides such as neohesperidine dihydrochalcone (NHDC), glycyrrhizin, glutamate, etc., alone or mixtures thereof. These substances insure a great lingering of the sweet taste and cover the bitter and metallic aftertaste of saccharine and its salts.

The powdered masking agent according to the invention can also contain other ingredients in small quantities, such as taste enhancers, sodium glutamate, nucleotides (sodium inosinate and guanylate), maltol and ethylmaltol, etc. These ingredients are included in "microingredients" which can enter the intermediate formulation of the medicament or premix which can also contain vitamins, oligo-elements, or even other medicinal substances administered preventively or prophylactically. These substances are generally calculated to be present in an amount of 75 to 150 g per kg in the final medicament.

To prepare the masking agent according to the invention, its various constituents may be dissolved together in water at a temperature between 40 and 70° C., or alternatively, dissolution may be carried on in two separate batches which are thereafter mixed together, temperature being maintained in the above range.

Typical parameters for spray-drying at atmospheric pressure are as follows:
  incoming air temperature: 175 to 200° C.
  outgoing air temperature: 75 to 100° C.
  incoming pressure (nozzle or turbine): 150 to 180 bars
  flow rate of nozzle: 250 to 290 l/h
  nozzle opening diameter: 1.15 to 1.25 mm The powder falling down to the bottom of the spay-drying tower may be collected on a fluidized bed and then spayed in a continuous process with water (1 to 2% of water with regard to the water, in weight).

Said water may comprise motting or gelifying agent in a concentration of 1 to 2% by weight, such as gums alginates, carraghenates, cellulose derivatives, methyl or carboxymethycellulose for instance. Such a moistened powder has an improved dissolution in water, if it is to be dissolved later in a liquid.

The masking agent according to the invention can be used with a large number of pharmaceutical or therapeutic products having unpleasant taste, belonging to many different categories thereof, for example antibiotics, analgesics, antitussive, anti-malaria, antiinflamatory, anti-nausea, anti-asmathic, laxative, expectorant, decongestive, hypocholestoral, or anti-histaminic agents, etc., or alimentary products of dietetic, pharmaceutical or parapharmaceutical nature, such as appetite suppressers, nutritional supplements or vitamin supplements, etc. For further details, reference is made to EP 0 371 584 cited above which provides a long, but non-exhaustive list of pharmaceutical products having unpleasant tastes to be masked.

The powdered masking agent according to the invention can be prepared very easily, on the basis of a technology well known in human foodstuff technology and in the technology of taste manufacturing, as "micronisation", i.e. atomizing and drying a liquid mixture, pulverized in an appropriate apparatus (spray drying). The apparatus can take the form of a tower, in which the liquid mixture is fed from the top in a nozzle or in a turbine, the atomized powder being collected at the base of the tower. In some cases, if necessary, the tower can be filled with an inert gas to prevent oxidation phenomena.

To use the powdered masking agent according to the invention care should be taken to provide a homogeneous mixture between the active principle and the excipient which is usually included. On the basis of usual values, this allows to constitute a final medicament having a quantity of sweetener of the order of 30 to 90 g/kg and a quantity of potentiator from 1.5 to 6.3 g/kg on the basis of a mean dosage of the active agent from 20 to 70 g/kg, these values evidently being extremely variable according to the composition of the masking agent and the active principle considered. It should be understood that, as the masking agent according to the invention is perfectly homogeneous and the particle size of the masking agent is sufficiently fine, there will be no difficulty to obtain a masking formulation or a final medicament, which are also both perfectly homogeneous.

According to another embodiment, the invention relates to a medicament in powder form in the form of an intimate mixture whereof the sapid agent/potentiator distribution is substantially homogeneous, non-statistical, and whereof the proportion of sapid agent relative to the potentiator is substantially constant and equal in all powder particles.

Such a medicament is prepared by mixing a solution of a sapid agent and a potentiator followed by spray drying this mixture to produce a powder.

From this starting medicament, one can then, if desired, and using conventional techniques, prepare a final medicament in the form of granules, tablets, effervescent powders, pills, lozenges and chewable gum, or syrups.

The invention will be better understood by reference to the following non-limiting examples. These examples will be followed by comparative examples in order to highlight the advantages of the invention which are:
  an even masking effect;
  the possibility to add adjuvants in even quantities too;
  an excellent conservation stability, better than that of coarse masking agent whose two constitutive powders, with very different particle sizes, tend with time to segregate or to sediment;
  the fact that because of its amorphous crystalline structure and its relative humidity of 2 to 4% (compared to 5 to 15% for sodium saccharinate), the masking agent according to the invention flows freely; it is therefore not necessary to add anticlodding agents such as silica and, because of this, is fully soluble in water without leaving residues, the solubility being instantaneous.

EXAMPLES 1 TO 9

A solution is prepared from one or more sweetener(s) by introducing 900 liters of water in a vat, then heating to 60_C. 1000 kg of sweetener(s) is then slowly added, the solution being agitated during 30 minutes until complete dissolution (the solution becomes transparent).

Meanwhile, in a small vat filled with 100 liters of water heated to 70_C., the potentiator(s) is (are) slowly added, in a quantity corresponding to the desired sweetener/potentiator proportion for the masking agent to be prepared, then the product is allowed to dissolve for 30 minutes.

The potentiator(s) solution is slowly added to the sweetening solution.

When the solution becomes transparent, a spray-drying operation is performed in a column under the following working conditions:

| | |
|---|---|
| Solution temperature | 60° C. |
| Incoming air temperature | 190° C. |
| Outgoing air temperature | 100° C. |

Atomizing turbine rotation speed: 15'000 rpm to 20'000 rpm.

The turbine may be replaced by an atomization nozzle with a diameter of 1.19 mm, working under 150 bars with a flow rate of 258 l/h.

A masking agent according to the invention is thus obtained, presented under the form of a fine homogeneous powder having a particle size with a Gaussian distribution comprised between 10 and 100 µm with a mean of 48.5 µm and comprising around 75,000,000 particles or grains per gram. This powder is water-soluble. It can be packaged in big bags for handling. Even after a long storage, no segregation may be noticed in bags and the powder remains homogenous, which in turn means that their masking power remains homogenous as well.

The following powdered masking agents have thus been produced, with sweeteners and potentiators and according to the proportions expressed in weight parts, as follows:

| EXAMPLES | SWEETENERS | POTENTIATORS | PROPORTIONS |
|---|---|---|---|
| 1 | Sodium saccharinate/ Aspartam | NHDC | 70/25/5 |
| 2 | Sodium saccharinate/ Acesulfam K | NHDC | 35/60/5 |
| 3 | Aspartam/ Acesulfam | NHDC | 10/86/4 |
| 4 | Sodium saccharinate/ Aspartam | NHDC/ Glycyrrhin | 70/25/2/3 |
| 5 | Sodium saccharinate/ Acesulfam K | Glycyrrhin/ Maltol | 40/53/3/4 |
| 6 | Sodium saccharinate/ Acesulfam K | Glycyrrhin/ Ethyl-Maltol | 42/53/3/2 |
| 7 | Sodium saccharinate/ Acesulfam K | NHDC/ Glycyrrhin/ Ethyl-Maltol | 40/53/2/3/2 |
| 8 | Acesulfam K | NHDC/ Glycyrrhin | 95/2/3 |
| 9 | Aspartam/ Acesulfam K | NHDC/ Glycyrrhin/ Ethyl-Maltol | 10/84/2/2/2 |

EXAMPLES 10 TO 12 AND COMPARATIVE EXAMPLES

Tablets and effervescent powders of paracetamol, an antipyretic antalgic agent having a bitter taste, are prepared by dry mixing. Each tablets contains 500 mg of paracetamol in 0.6 g tablets, or 150 mg of effervescent powder per 0.3 g sachet, using the above masking agents of Examples 1, 5 and 9 and respectively using sodium saccharinate of 40–80 Mesh.

| | Ex. 10 % | Ex. 11 % | Ex. 12 % | Ex. 13 % |
|---|---|---|---|---|
| Paracetamol | 96.15 | 94.20 | 92.30 | 96.15 |
| Example 1 | 3.85 | | | |
| Example 5 | | 5.80 | | |
| Example 9 | | | 7.70 | |
| Comparative Example: Sodium Saccharinate 40–80 Mesh | | | | 3.85 |

A tasting test is then carried out for each of these mixtures in 30 ml of water.

Example 10—Contains 500 mg of paracetamol+20 mg of masking agent.

Example 11—Contains 500 mg of paracetamol+30 mg of masking agent.

Example 12—Contains 500 mg of paracetamol+42 mg of masking agent

Comparative Example—Contains 500 mg of paracetamol+ 20 mg of sodium saccharinate 40–80 Mesh.

The results obtained are as follows:

Example 10: sweet taste, followed by a slight bitter taste which appears after 30 seconds and disappears after 2 minutes; thereafter the sweet taste continues and disappears after 3 minutes 30 seconds.

In this Example, there are about 75,000,000 particles per g. In a 0.6 g tablet there are therefore 1,500,000 particles, which results in a very great "covering" effect relative to the active principle particles.

Example 11: sweet taste close to that of saccharose followed by a slight bitter taste which appears after 45 seconds and disappears after 1 minute 45 seconds; thereafter the sweet taste continues and disappears after 3 minutes 6 seconds.

In this Example, there are also about 75,000,000 particles per g. In a 0.6 g tablet, there are therefore 2,250,000 particles.

Example 12: sweet taste very close to that of saccharose followed by a very slight bitter taste which appears after 80 seconds and disappears after 1 minute 40 seconds; thereafter the sweet taste continues and disappears after 4 minutes 25 seconds.

In this Example, there are still 75,000,000 particles per g. In a 0.6 g tablet, there are 31,500,000 particles.

Comparative Example: sweet and bitter taste; the bitter taste appears after 10 seconds, thereafter the sweet taste disappears after 1 minute and the bitter taste persist during 2 minutes 15 seconds.

In this Example, with a traditional masking agent, there are therefore 60,000 particles per g, namely 1,200 particles per 0.6 g tablet, producing a weak masking effect relative to the active principle.

This comparison clearly demonstrates the masking effects according to the invention, compared to a traditional sweetening agent based on sodium saccharinate.

EXAMPLE 13

The procedure of the previous Examples is followed, but substituting quinine chlorohydrate and using the masking agent of Example 6 based on paracetamol to produce a tablet containing 500 mg of quinine hydrochloride and 36.48 mg of masking agent.

When being subjected to tasting, a sweet taste accompanied by a liquorice and caramel flavor and a slight bitter taste are noted; this bitter taste decreases and disappears after 3 minutes 30 seconds and the sweet taste disappears after 3 minutes 45 seconds.

EXAMPLES 14 TO 20

The mixtures of Examples 10 to 12 (and the comparative Example) are statistical mixtures. To obtain non statistical mixtures and consequently optimize the masking effect, all of the constituents of these mixtures (sweetening agents, potentiators, active principles) are, at the beginning of processing, intimately bound into a micro particle using the same fabrication technology as for the masking agents according to the invention.

A solution is thus prepared of one or several sweetening agents by adding 900 liters of water into a vat, then heating to 60° C. 1000 kg of the sweetening agent(s) is then slowly added, and the solution agitated for 30 minutes until complete dissolution (whereupon the solution becomes transparent).

Meanwhile, in a small vat filled with 100 liters of water warmed to 70° C., the potentiator(s) is/are added in a quantity corresponding to the desired sweetener/potentiator proportion for the masking agent being prepared. Then the product is allowed to dissolve during 30 minutes.

The active principle is then added, previously dissolved in a sufficient quantity of water, and the mixture is atomized in an atomizing tower in the same conditions as the preceding examples.

This process is carried out with quinine hydrochloride, an antimalaria agent having a very strong bitter taste.

|  | Example 14 % | Example 15 % | Example 16 % |
|---|---|---|---|
| Quinine hydrochloride | 95.5 | 92.8 | 93.2 |
| Masking agent of Example 1 | 4.6 | | |
| Masking agent of Example 3 | | 7.2 | |
| Masking agent of Example 6 | | | 6.8 |

The % of the masking agent of Ex. 1 are comprised between 3.3 and 6.2%

The % of the masking agent of Ex. 3 are comprised between 6.5 and 8.2%

The % of the masking agent of Ex. 6 are comprised between 5.4 and 7.7%

A tasting procedure is then carried out on each of these mixtures in 30 ml of water.

Example 14—Contains 500 mg of quinine hydrochloride+ 23.56 mg of masking agent.

Example 15—Contains 500 mg of quinine hydrochloride+ 36.65 mg of masking agent.

Example 16—Contains 500 mg of quinine hydrochloride+ 36.48 mg of masking agent.

The results obtained are as follows:

Example 14: a sweet and slightly bitter taste appear at the same time, whereafter the bitter taste disappears after 3 minutes 45 seconds, whereas the sweet taste is extended until 4 minutes 25 seconds.

Example 14: pleasant sweet and slightly bitter taste; the bitter taste diminishes and disappears after 2 minutes 30 seconds, whereas the sweet taste is extended until 3 minutes 40 seconds.

Example 16: a sweet taste accompanied with a liquorice and caramel taste and a slight bitter taste, smoother than in the test of Examples 13 and 14; the bitterness diminishes and disappears after 3 minutes, thereafter the sweet taste is extended during 4 minutes 30 seconds.

Once again, this comparison clearly demonstrates the masking effects according to the invention.

The same procedure is carried out with dextromethorphan, an anti-tussive agent which also has a bitter taste

|  | Example 17 % | Example 18 % | Example 19 % | Example 20 % |
|---|---|---|---|---|
| Dextromethorphan | 94.2 | 95.5 | 96.0 | 91.2 |
| Masking agent of Example 2 | 5.8 | | | |
| Masking agent of Example 4 | | 4.5 | | |
| Masking agent of Example 7 | | | 4.0 | |
| Masking agent of Example 8 | | | | 8.8 |

Ex. 2 comprises between 4.2 and 6.5% of masking agent
Ex. 4 comprises between 3.5 and 5.5% of masking agent
Ex. 7 comprises between 3.2 and 5.0% of masking agent
Ex. 8 comprises between 7.0 and 9.5% of masking agent Instead of an unpleasant bitter taste, a medicament containing this anti-tussive agent had a sweet taste whose general fragrance varies from one Example to another.

The invention has been described here by way of example for the masking of bitter tastes which are the most unpleasant perceptions and the most difficult ones to mask. It applies a fortiori to other less aggressive gustatory and olfactive perceptions, such as acid and salty tastes.

What is claimed is:

1. A masking agent for pharmaceutical tastes, comprising a mixture of a sapid agent and an enhancer, in the form of an intimate mixture wherein the sapid agent/enhancer distribution is substantially homogeneous, non-statistical, and wherein the portion of sapid agent relative to the enhancer is substantially constant and equal in all powder particles, and wherein the sapid agent is drawn from a class that includes sweeteners including methyl-, ethyl- and carboxyl (m)ethyl celluloses, pectins, carraghenates, alginates, sodium and calcium saccharinates, saccharine, aspartylphenylalanine, aspartam, acesulfams, acesulfam K cyclamates, steviosides, and mixtures thereof, and the enhancer is drawn from a class that includes proteins of vegetable origin, thaumatin, glycosides, neohesperidin dihydrochalcone (NHDC), glycyrrhizin, maltols, ethyl maltol glutamates, and mixtures thereof.

2. The masking agent according to claim 1, wherein said agent has a grain size comprised between 10 and 100 μm, with a Gaussian distribution, and/or the proportion of sapid agent/enhancer is comprised between 97/3 and 90/10, expressed in parts by weight.

3. The masking agent according to claim 1, wherein the sapid agent comprises a sweetener.

4. The masking agent according to claim 3, wherein the sweetener is selected from the group consisting of sodium saccharinates, calcium saccharinates, saccharine, aspartylphenylalanine, acesulfam, cyclamates, stevioside, and mixtures thereof; and the enhancer is selected from the group consisting of thaumatin, neohesperidin dihydrochalcone (NHDC), glycyrrhizin, and mixtures thereof.

5. A method of producing a masking agent according to claim 1, comprising the steps of: preparing a mixture of a solution of a sapid agent and an enhancer, followed by spray drying this mixture to produce a powder.

6. A pharmaceutical product including the masking agent according to claim 1.

7. A medicament comprising an active agent and a masking agent according to claim 1, and optionally a pharmaceutically acceptable excipient.

8. A medicament in powder form, comprising in the form of an intimate mixture wherein the sapid agent/enhancer distribution is substantially homogenous, non-statistical, and wherein the proportion of sapid agent relative to the enhancer is substantially constant and equal in all powder particles, and wherein the sapid agent is drawn from a class that includes sweetners including methyl-, ethyl- and carboxy(m)methyl celluloses, pectins, carraghenates, alignates, sodium and calcium saccharinates, saccharine, aspartylphenylalanine, aspartam, acesulfams, acesulfam K cyclamates, steviosides, and mixtures thereof, and the enhancer is drawn from a class that includes protiens of vegetable origin, thaumatin, glycosides, neohesperidin dihydrochalcone (NHDC), glycyrrhizin, maltols, ethyl maltol glutamates, and mixtures thereof.

9. The medicament according to claim 8, wherein said medicament has a grain size comprised between 10 and 100 μm, with a Gaussian distribution, and/or the proportion of sapid agent/enhancer is comprised between 97/3 and 90/10, expressed in parts by weight.

10. The medicament according to claim 8, wherein the sapid agent comprises a sweetener.

11. The medicament according to claim 10, wherein the sapid agent comprises a sweetener selected from the group consisting of sodium saccharinates, calcium saccharinates, saccharine, aspartyl-phenylalanine, acesulfam, cyclamates, stevioside, and mixtures thereof; and the enhancer is selected from the group consisting of thaumatin, neoesperidin dihydrochalcone (NHDC), glycyrrhizin, and mixtures thereof.

12. A method of producing a powdered medicament according to claim 8, comprising the steps of: preparing a mixture of a solution of a sapid agent and an enhancer, followed by spray drying this mixture to produce a powder.

13. A medicament in the form of granules, tablets, effervescent tablets, pills, lozenges or chewable gum, obtained from a medicament according to claim 7.

14. A medicament in the form of granules, tablets, effervescent tablets, pills, lozenges or chewable gum, obtained from a medicament according to claim 8.

15. The method according to claim 5, in which the powder is collected on a fluidized bed and sprayed with 1 to 2% of water in weight.

16. The method according to claim 15, in which the spraying water contains between 1 and 2% in weight of a gum, an alginate, a carraghenate or a cellulose derivative.

17. A masking agent for pharmaceutical tastes, comprising a mixture of a sapid agent and a potentiator, in the form of an intimate mixture whereof the sapid agent/potentiator distribution is substantially homogeneous, non-statistical, and wherein the proportion of sapid agent relative to the potentiator is substantially constant and equal in all powder particles, said masking agent having a grain size comprised between 10 and 100 m with a Gaussian distribution, and wherein the sapid agent is drawn from a class that includes sweeteners including methyl-, ethyl- and carboxyl(m)ethyl celluloses, pectins, carraghenates, alginates, saccharinates, saccharine, aspartyiphenylalanifle, aspartam, acesulfams, acesulfam K cyclamates, steviosides, and mixtures thereof, and the enhancer is drawn from a class that includes proteins of vegetable origin, thaumatin, glycosides, neohesperidin dihydrochalcone (NHDC), glycyrrhizin, maltols, ethyl maltol glutamates, and mixtures thereof.

18. The masking agent according to claim 17, characterized in that the proportion of sapid agent/potentiator is comprised between 97/3 and 90/10, expressed in parts by weight.

* * * * *